(12) United States Patent
Satoh

(10) Patent No.: US 6,426,993 B1
(45) Date of Patent: Jul. 30, 2002

(54) ENERGY DISPERSION-TYPE X-RAY DETECTION SYSTEM

(75) Inventor: Masao Satoh, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/934,006

(22) Filed: Aug. 20, 2001

(30) Foreign Application Priority Data

Aug. 25, 2000  (JP) ........................................ 2000-254968

(51) Int. Cl.$^7$ ............................................ G01N 23/223
(52) U.S. Cl. ........................................................ 378/45
(58) Field of Search ................................ 378/44–50, 83

(56) References Cited

U.S. PATENT DOCUMENTS 5,978,442 A * 11/1999 Kuwabara ..................... 378/46
6,292,532 B1 * 9/2001 Kawahara et al. ............ 378/45

* cited by examiner

Primary Examiner—Craig E. Church
(74) Attorney, Agent, or Firm—Adam & Wilks

(57) ABSTRACT

In order to realize accurate analysis with a fluorescent X-ray analyzer characterized by being non-destructive and non-contacting, in a short period of time, there is provided a common X-ray generating source, a collimator for focusing primary X-rays, and, as an energy dispersion type X-ray detection system for analyzing fluorescent X-rays as a means of elemental analysis, an energy dispersion type detector where a sensor with a low count rate but having superior energy resolution and a sensor with poor energy resolution but having a superior count rate are juxtaposed. In a method where a detector signal with superior energy resolution is utilized as foreseeable information in quantitative analysis and then utilized in qualitative analysis and a detection signal with a superior count rate is utilized in quantitative analysis, after a latter stage comprising a preamplifier of the detector, a linear amplifier and pulse height analyzer is provided individually, and qualitative and quantitative spectral processing is carried out using a common control and computing unit.

2 Claims, 2 Drawing Sheets

ENERGY DISPERSION-TYPE X-RAY DETECTION SYSTEM

BACKGROUND OF THE INVENTION

The present invention relates to an energy dispersion-type X-ray detector utilized in energy dispersion-type X-ray analyzers and X-ray analyzers fitted with electron microscopes.

With energy dispersion-type fluorescent X-ray analyzers of the related art, selections are made as to whether to give priority to resolution or to count rate by utilizing an Si semiconductor detector with superior energy resolution and then switching over the time constant of a count circuit. However, there are no fluorescent X-ray analyzers capable of utilizing high resolution information to perform measurements at a high count rate, i.e. to take measurements with a high degree of precision over a short period of time.

The energy dispersion detector has a detection performance whereby the resolution and the count rate conflict with each other. Typically, when the device thickness and surface area of the sensor are increased in order to increase the count rate, the resolution either deteriorates or does not function at all.

In the related art, when elemental analysis or thin film measurements are carried out using a fluorescent X-ray analyzer, and the sample is not as-yet known, qualitative analysis is required. This situation requires a high resolution spectrum where each peak overlaps as little as possible, and a silicon drift chamber or semiconductor detector is therefore used. Conversely, in the case of quality management when measuring thin films, or cases where the structural composition is already known from the point of view of quality management and it is only wished to perform composition measurements, then proportional counter tubes having high count rate characteristics are used with the aim of keeping statistical errors regarding the strength of the X-rays small. However, after performing qualitative analysis using a high-resolution system in order to identify as yet unknown samples and implement high-precision measurements, it is necessary to perform the measurements again using a high resolution system taking the identified element as foreseeable information.

SUMMARY OF THE INVENTION

An energy dispersion-type detector is prepared where a sensor with a low count rate but with a superior energy resolution and a sensor with poor energy resolution but with a superior count rate are positioned in a juxtaposed manner. A method is then adopted where a signal for the sensor with superior energy resolution is utilized as foreseeable information in quantitative analysis and then utilized in qualitative analysis, and a signal for the sensor with a superior count rate is utilized in quantitative analysis. The latter stage of the sensors comprise individual preamplifiers, linear amplifiers, and pulse height analyzers, and processing is performed on spectrums in both a qualitative and quantitative manner using a common control and computing unit. This means that high resolution spectra for use in qualitative analysis and high count rate spectra for use in quantitative analysis can be obtained simultaneously in a short period of time.

DETAILED DESCRIPTION OF THE PREFERRED EMBODIMENT

Figure 1:
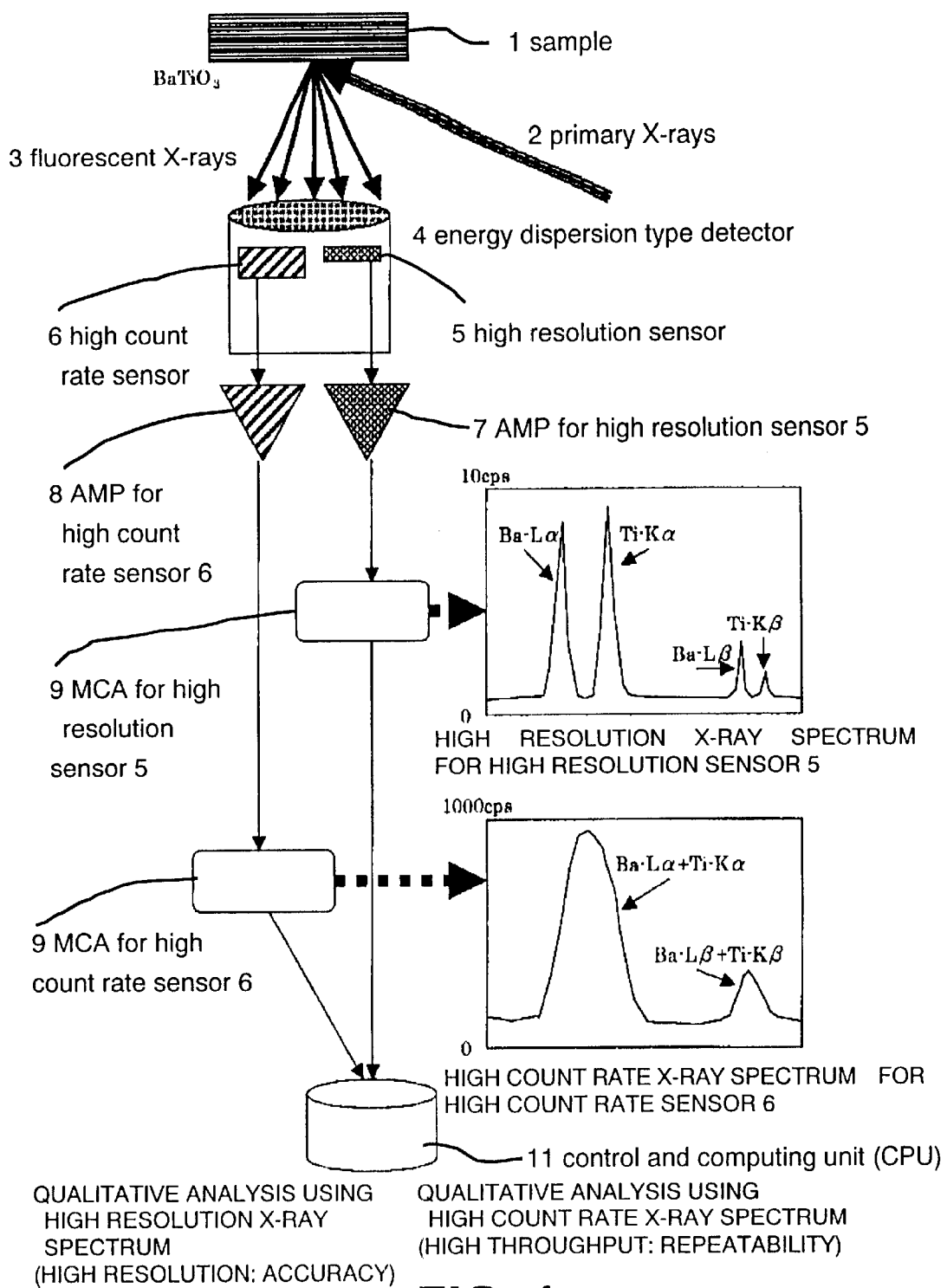
FIG. 1 is a view showing a first embodiment of the present invention.

FIG. 1 shows an embodiment of an energy dispersion-type detection system enabling processing of data obtained while simultaneously detecting a high resolution X-ray spectrum and a high counting efficiency X-ray spectrum, with dimensions being small in both cases. A sample 1 is irradiated with primary X-rays 2, and fluorescent X-rays 3 generated as a result are detected by an energy dispersion-type X-ray detector 4. A high resolution sensor (first sensor) 5 characterized by high resolution such as, for example, a silicon drift chamber (SDD-1) with the time constant of a count circuit set to be long and utilizing a high resolution characteristic, or a microcalorimeter (MC) or a Josephson junction superconducting X-ray detector (STJ's), and a high count rate sensor (second sensor) 6 characterized by a high count rate such as, for example, a high count rate silicon drift chamber (SDD-2) with the time constant of a count circuit set to be short, or a high purity Si semiconductor detector or Si(Li) semiconductor detector (SSD) are provided at an energy dispersion type X-ray detector 4. Then, processing is performed on spectrums in both a qualitative and quantitative manner using a common control and computing unit 11.

When a silicon drift chamber (SDD-1) is utilized as the high resolution sensor 5, the resolution with respect to the Mn-Ka line (5.9 keV) is 150 eV or less, and the count rate is in the order of 1000 cps. When a microcalorimeter (MC) or Josephson junction superconducting X-ray detector (STJ's) is utilized as the high resolution sensor 5, resolution (FWHM) with respect to the Mn-Ka line (5.9 keV) is a few tens of eV or less, and the count rate is from a few hundred cps to a few thousand cps.

When a silicon drift chamber (SDD-1) is utilized as the high count rate sensor 6, the resolution (FWHM) with respect to the Mn-Ka line (5.9 keV) is 250 eV, with a count rate in the order of a few hundred thousand cps. When a high purity Si semiconductor detector or Si (Li) semiconductor detector (SSD) is utilized in combination with a digital signal processing system, the resolution (FWHM) with respect to the Mn-Ka line (5.9 keV) is 200 eV or less, with the count rate being in the order of a few tens of thousands of cps. With the silicon drift chamber (SDD), high energy detection is not possible because of the inverse relationship with device thickness, and a detection rate in the order of 15% is obtained at 25 keV. However, with a high purity Si semiconductor detector or Si (Li) semiconductor detector (SSD), a detection rate in the order of 75% can be obtained at 25 keV.

Figure 2:
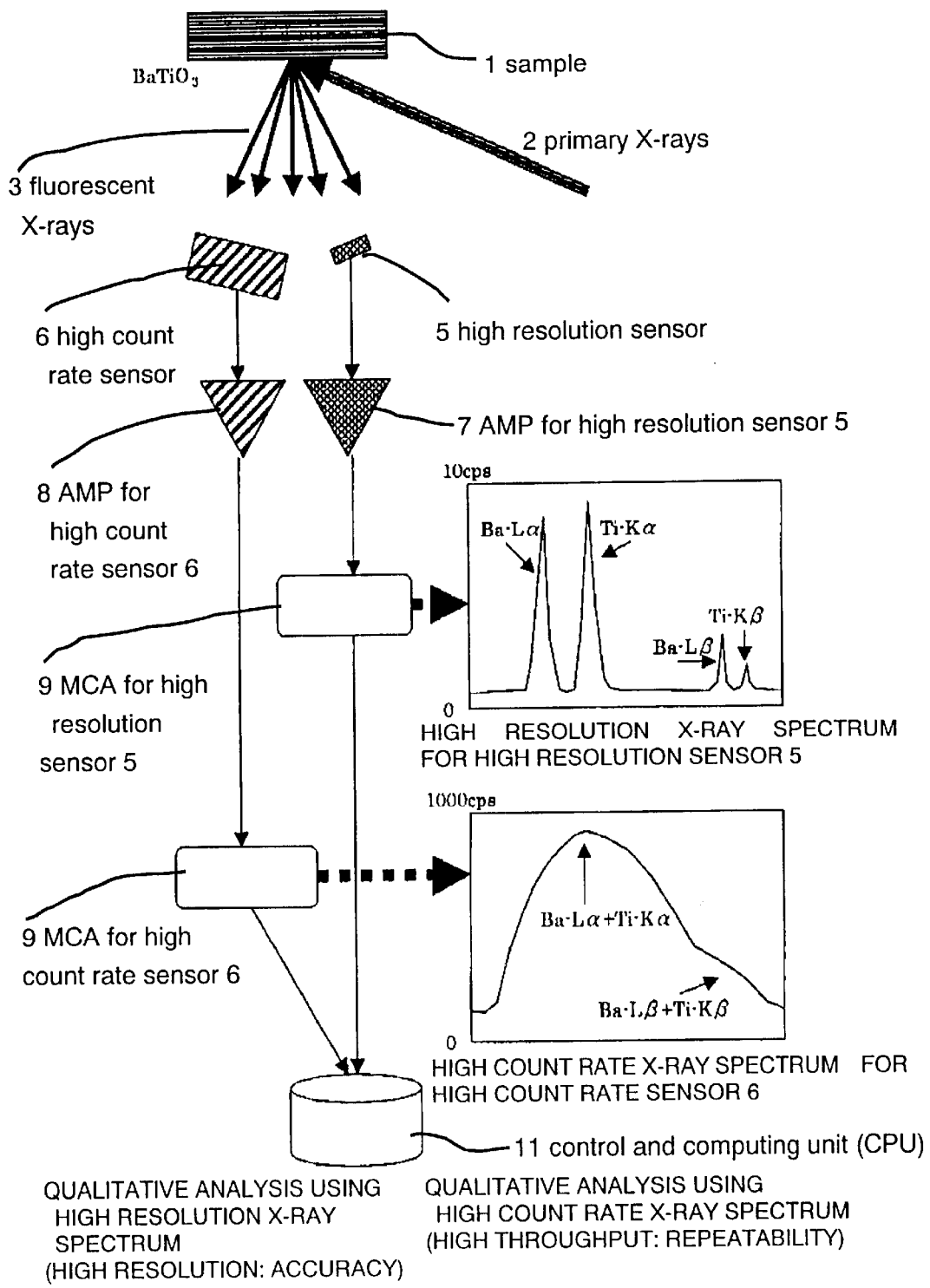
FIG. 2 is a view showing a further embodiment of the present invention.

Further, an embodiment where, rather than providing an integrated unit as the high count rate sensor 6, there is separately provided a proportional counter tube with a resolution in the order of 1 keV but a count rate in the order of a few hundred thousand cps and, when a scintillation counter is utilized, a poor resolution of a few keV and a count rate of a few hundred thousand cps, is shown in FIG. 2.

FIG. 1 also demonstrates the X-ray spectrum for the case where a microcalorimeter (MC) and semiconductor (SSD) are utilized as the high resolution sensor 5. High resolution X-ray spectra and high count rate X-ray spectra illustrate the respective sensor outputs when the sample 1 is barium titanate. A microcalorimeter (MC) giving a resolution (FWHM) in the order of 10 eV for a Ba-La line (4.47 keV)

and a Ti-Kb line (4.51 keV) can be provided separately, but it is not possible to provide a semiconductor detector with a resolution (FWHM) in the order of 180 eV separately. This means that qualitative analysis using X-ray spectra from high resolution sensor 5 having a high resolution characteristic or quantitative analysis using spectra of the high count rate sensor 6 having a difference in count rate of two orders of magnitude different is possible.

When a detector with a superior count rate is used in the related art, structural elements are inputted as foreseeable information and overlapping peaks are separated and analyzed. When a high resolution detector is utilized, the measuring time is extended and the intensity of the X-rays is multiplied up to a prescribed X-ray intensity so as to give the required precision. However, with the present invention, while analysis time is made short using a single system accurate analysis is still possible.

What is claimed is:

1. An energy dispersion-type X-ray detection system comprising an energy dispersion-type X-ray detector, said energy dispersion-type X-ray detector comprising:

a silicon drift chamber utilizing a count circuit with the time constant set to be long, and a microcalorimeter or a Josephson junction superconducting X-ray detector as a first sensor that is small in dimension, has a poor count rate, but has superior energy resolution; and a silicon drift chamber utilizing a count circuit with the time constant set to be short, and a high-purity Si semiconductor detector or an Si (Li) semiconductor detector as a second sensor having poor energy resolution but having a superior count rate, with the first and second sensors being arranged integrally in a juxtaposed manner, wherein a system is adopted where a signal from the first sensor with superior energy resolution is utilized as foreseeable information in quantitative analysis and then utilized in qualitative analysis, and a signal from the second sensor of superior count rate is utilized in quantitative analysis, with the latter stages of the sensors comprising individual preamplifiers, linear amplifiers, and pulse-height analyzers, the processing on spectrums being performed in both a qualitative and quantitative manner using a common control and computing unit.

2. An energy dispersion-type X-ray detection system wherein a silicon drift chamber, microcalorimeter or Josephson junction-type superconducting X-ray detector taken as a first sensor with a low count rate and superior energy resolution, and a proportional counter tube or scintillation counter taken as a second sensor with poor energy resolution and a superior count rate are located in a juxtapositioned manner, wherein a system is adopted where a signal from the first sensor with superior energy resolution is utilized as foreseeable information in quantitative analysis and then utilized in qualitative analysis, and a signal from the second sensor with a superior count rate is utilized in quantitative analysis, with the latter stage of the sensors comprising individual preamplifiers, linear amplifiers, and pulse height analyzers, and processing is performed on spectrums in both a qualitative and quantitative manner using a common control and computing unit.

* * * * *